United States Patent [19]

Baker et al.

[11] Patent Number: 5,242,927
[45] Date of Patent: Sep. 7, 1993

[54] PRODRUGS FOR OXADIAZOLE MUSCARINIC AGONISTS

[75] Inventors: Raymond Baker, Much Hadham; John Saunders; Angus M. MaCleod, both of Bishop's Stortford; Graham A. Showell, Welwyn Garden City, all of England

[73] Assignee: Merck Sharp & Dohme Limited, Hoddesdon, England

[21] Appl. No.: 220,209

[22] Filed: Jul. 18, 1988

[30] Foreign Application Priority Data

Jul. 23, 1987 [GB] United Kingdom ................ 8717446

[51] Int. Cl.$^5$ ...................... A61K 31/44; C07D 413/04
[52] U.S. Cl. .................................... 514/299; 514/304; 514/305; 514/340; 514/364; 546/112; 546/125; 546/133; 546/137; 546/277; 548/133
[58] Field of Search ............... 546/133, 137, 277, 112, 546/125; 514/305, 340, 364, 299, 304; 548/133

[56] References Cited

U.S. PATENT DOCUMENTS

| | | | |
|---|---|---|---|
| 4,599,344 | 7/1986 | Morgan | 514/305 |
| 4,608,378 | 8/1986 | Falch et al. | 514/302 |
| 4,617,150 | 10/1986 | Hubschwerlen et al. | 540/364 |
| 4,704,385 | 11/1987 | Ponsford et al. | 514/210 |
| 4,988,706 | 1/1991 | Hadley et al. | 514/299 X |
| 5,043,343 | 8/1991 | Wyman | 546/112 X |
| 5,091,397 | 2/1992 | Wadsworth et al. | 514/364 X |

FOREIGN PATENT DOCUMENTS 2393097  9/1987  European Pat. Off. .
2843887  4/1980  Fed. Rep. of Germany .

OTHER PUBLICATIONS

P. Saverberg, et al., *J. Med. Chem.* 29 1004 (1986).
M. Bock et al., *J. Med. Chem.* 29, 1540 (1986).
B. Ringdahl, et al., *J. Med. Chem.* 31, 160–164 (1988).
Higuchi, T., et al., *Prodrugs as Novel Drug Delivery Systems*, Acs, Wa., 1975, p. 15.

*Primary Examiner*—Mary C. Lee
*Assistant Examiner*—Fiona T. Powers
*Attorney, Agent, or Firm*—Robert J. North; Joseph F. DiPrima

[57] ABSTRACT

A class of novel oxadiazoles, substituted on one of the ring carbon atoms with a non-aromatic azacyclic or azabicyclic ring and on the other ring carbon atom with a substituent which is convertible in vivo to an amino group, are potent muscarinic agonists, and exhibit improved CNS penetrability and duration of action compared with the corresponding amino compounds. The compounds are therefore useful in the treatment of neurological and mental illnesses.

7 Claims, No Drawings

PRODRUGS FOR OXADIAZOLE MUSCARINIC AGONISTS

The present invention relates to a class of oxadiazole compounds which stimulate central muscarinic acetylcholine receptors and are useful in the treatment of neurological and mental illnesses whose clinical manifestations are due to involvement of specific populations of cholinergic neurones. Such diseases include presenile and senile dementia (also known as Alzheimer's disease and senile dementia chorea, tardive dyskinesia, hyperkinesia, mania and Tourette Syndrome. Alzheimer's disease, the most common dementing illness, is a slowly progressive neurological disorder characterised by marked deficits in cognitive functions including memory, attention, language and visual perception capabilities. The compounds of this invention are also useful analgesic agents and therefore useful in the treatment of severe painful conditions such as rheumatism, arthritis, and terminal illness.

Most muscarinic agonists, including acetylcholine itself, are quaternary ammonium compounds incapable of penetrating the blood-brain barrier to any clinically significant extent following peripheral (e.g. oral) administration. Such agents fail to stimulate the desired central sites but instead induce undesired side-effects mediated exclusively by peripherally-located muscarinic acetylcholine receptors.

Published European Application No. 239309 discloses a class of oxadiazoles, substituted on one of the ring carbon atoms thereof with a non-aromatic azacyclic or azabicyclic ring system; and substituted on the other ring carbon with a substituent which is inter alia the amino group. Those compounds are potent muscarinic agonists but, being either secondary or tertiary amines with physiochemical properties (lipophilicity and pKa) consistent with CNS penetrability, can stimulate those central sites implicated in neurodegenerative disorders.

A class of prodrugs of the compounds of published European Application No. 239309 has now been discovered which exhibit improved CNS penetrability and duration of action compared with the parent compounds.

Accordingly, the present invention provides an oxadiazole compound or a salt thereof, said compound being substituted on one of the ring carbon atoms thereof with a non-aromatic azacyclic or azabicyclic ring system; and substituted on the other ring carbon atom with a substituent which is convertible in vivo to an amino group.

The novel compounds of this invention may be represented by structural formula (I):

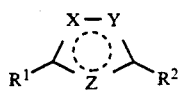

or a salt thereof; wherein one of X, Y or Z is an oxygen atom and the other two are nitrogen atoms, and the dotted circle represents aromaticity (two double bonds) thus forming a 1,3,4-oxadiazole or 1,2,4oxadiazole nucleus; $R^1$ represents a non-aromatic azacyclic or azabicyclic ring system; and $R^2$ represents a substituent which is convertible in vivo to an amino group.

Preferably the oxadiazole ring is a 1,2,4-oxadiazole.

The azacyclic or azabicyclic ring system is a non-aromatic ring system containing one nitrogen atom as the sole hetero atom. Suitably the ring system contains from 4 to 10 ring atoms, preferably from 5 to 8 ring atoms. The bicyclic systems may be fused, spiro or bridged. Examples of suitable ring systems include the following:

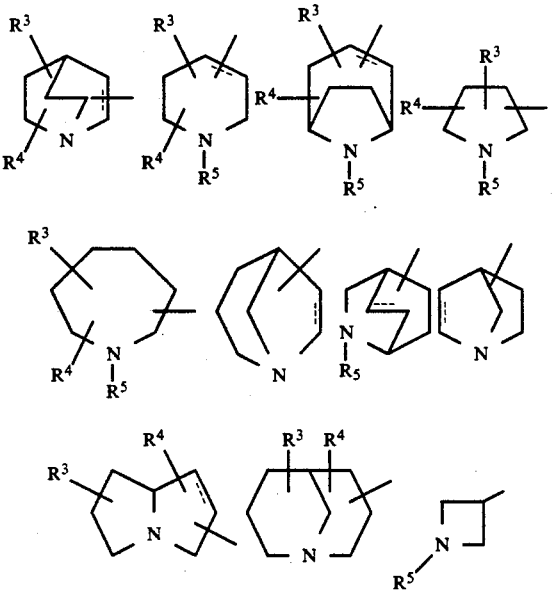

wherein the broken line represents an optional chemical bond;

the substituents $R^3$ and $R^4$ independently represent hydrogen, $C_{1-4}$ alkyl, halo, $C_{1-4}$ alkoxy, hydroxy or carboxy; or $R^3$ and $R^4$ together represent carbonyl; and the group $R^5$ represents hydrogen or $C_{1-4}$ alkyl. It will be appreciated that the nitrogen atom in the azacyclic or azabicyclic ring system will carry a lone pair of electrons.

Suitably the group $R^3$ is hydrogen or methyl; and $R^4$ is hydrogen, methyl or hydroxy. Preferably one or both of $R^3$ and $R^4$ is hydrogen.

Preferably the group $R^5$ represents hydrogen or methyl.

Suitably the azacyclic or azabicyclic ring system is a pyrrolidine, 1,2,5,6-tetrahydropyridine, quinuclidine or 1-azabicyclo[2.2.1]heptane ring, optionally substituted with methyl or hydroxy. A preferred azabicyclic ring system is quinuclidine, of structure:

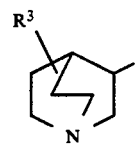

in particular where $R^3$ represents hydrogen, methyl or hydroxy.

Groups which are convertible in vivo to an amino group on the compounds of this invention may be readily ascertained by administering the compound to a human or animal and detecting, by conventional analytical techniques, the presence of the corresponding compound having an amino substituent in the urine of a human or animal. Examples of such groups include, for example, groups which are hydrolysable in vivo to an amino group such as amido and urethane substituents, in particular a group of formula —NH.Q, wherein Q represents CHO, COR or $CO_2R$, and R represents an optionally substituted hydrocarbon group.

The term 'hydrocarbon' includes groups having up to 20 carbon atoms, suitably up to 10 carbon atoms, conveniently up to 8 carbon atoms. Suitable hydrocarbon groups include $C_{1-8}$ alkyl, $C_{2-8}$ alkenyl, $C_{2-8}$ alkynyl, $C_{3-7}$ cycloalkyl, $C_{3-7}$ cycloalkyl($C_{1-6}$)alkyl, aryl, and aryl($C_{1-6}$)alkyl.

The alkyl group may be straight or branched chain and may contain, for example, up to 12 carbon atoms, suitably from 1 to 8 carbon atoms. In particular the group may be substituted methyl, ethyl, n- or iso-propyl, n-, sec-, iso- or tert-butyl, n- or iso-heptyl, or n- or iso-octyl.

Suitable cycloalkyl groups include cyclopentyl and cyclohexyl.

When used herein the term ,aryl, includes phenyl and naphthyl optionally substituted with up to five, preferably up to three, substituent groups.

Suitable optional substituents for the hydrocarbon group include $C_{1-6}$ alkyl, aryl, heterocyclic, amino, $C_{1-6}$ alkanoyl-amino, mono-, di- and tri-($C_{1-6}$)alkylamino, hydroxy, $C_{1-6}$ alkoxy, mercapto, $C_{1-6}$ alkylthio, heterocyclyl-thio, arylthio, sulphamoyl, carbamoyl, amidino, guanidino, nitro, hydroxy, chloro, bromo, fluoro, carboxy, $C_{1-6}$ alkoxycarbonyl, $C_{1-6}$ alkylcarbonyl, $C_{1-6}$ alkylcarbonyloxy, aryl-carbonyl and heterocyclylcarbonyl.

Where appropriate, two substituents may be combined to produce a ring system, for example a 1,2-phenylene system.

One sub-class of compounds within the scope of the present invention is represented by formula (II):

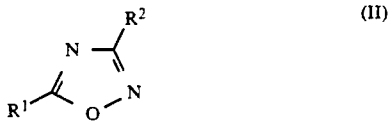

wherein $R^1$ and $R^2$ are as defined above. In particular, $R^1$ represents pyrrolidine, quinuclidine, tetrahydropyridine, piperidine, dehydrotropane, pyrrolizidine or 1-azanorbornane, any of which groups $R^1$ may be optionally substituted with $C_{1-3}$ alkyl or hydroxy. Preferably, $R^1$ represents 1,2,5,6-tetrahydropyridine, quinuclidine or 1-azanorbornane (i.e. 1-azabicyclo[2.2.1]heptane). In structure (II), suitably the group $R^2$ represents a group of formula —NH.Q, wherein Q represents CHO, COR or $CO_2R$, and R represents $C_{1-10}$ alkyl, phenyl, cyclohexyl, fluorenylmethyl, phenyl($C_{1-6}$)alkyl, cyclohexylmethyl or $C_{1-6}$ alkoxycarbonyl($C_{1-6}$)alkyl.

Specific compounds within the scope of this invention are :
3-[5-(3-octanoylamino-1,2,4-oxadiazol)-yl]quinuclidine;
3-[5-(3-benzoylamino-1,2,4-oxadiazol)-yl]quinuclidine;
3-[5-(3-isobutyrylamino-1,2,4-oxadiazol)-yl]quinuclidine;
3-[5-(3-(2,2-dimethylpropionyl)amino-1,2,4-oxadiazol)-yl]quinuclidine;
3-[5-(3-ethoxycarbonylamino-1,2,4-oxadiazol)yl]-quinuclidine;
3-[5-(3-iso-propoxycarbonylamino-1,2,4-oxadiazol)-yl]quinuclidine;
3-[5-(3-t-butoxycarbonylamino-1,2,4-oxadiazol)-yl]quinuclidine;
3-[5-(3-iso-butoxycarbonylamino-1,2,4-oxadiazol)-yl]quinuclidine;
3-[5-(3-(9-fluorenyl)methoxycarbonylamino-1,2,4-oxadiazol)-yl]quinuclidine;
3-[5-(3-cyclohexylmethoxycarbonylamino-2,4-oxadiazol)-yl]quinuclidine;
3-[5-(2,2-dimethylprop-1-oxycarbonylamino-1,2,4-oxadiazol)-yl]quinuclidine;
3-[5-(3-cyclohexyloxycarbonylamino-1,2,4-oxadiazol)-yl]quinuclidine;
3-[5-(3-octyloxycarbonylamino-1,2,4-oxadiazol)-yl]quinuclidine;
DL-3-[5-(3-(I-(3-n-pentyloxycarbonyl)-1-ethoxycarbonylamino)-1,2,4-oxadiazol)-yl]quinuclidine;
3-[5-(3-(3-phenylprop-1-oxycarbonylamino-1,2,4-oxadiazol)-yl]quinuclidine;
3-[5-(3,3-dimethylbut-1-oxycarbonylamino-1,2,4-oxadiazol)-yl]quinuclidine;
3-[5-(3-pent-3-yloxycarbonylamino-1,2,4-oxadiazol)-yl]quinuclidine;
3-[5-(3-(2-propylpent-1-yloxycarbonylamino)-1,2,4-oxadiazol)-yl]quinuclidine;
3-[5-(3-acetamido-1,2,4-oxadiazol)-yl]quinuclidine;
3-[5-(3-formamido-1,2,4-oxadiazol)-yl]-quinuclidine;
3-[5-(3-butyloxycarbonylamino-1,2,4-oxadiazol)-yl]quinuclidine;
3-[5-(3-(4-methyl-1-pentyloxycarbonylamino)-1,2,4-oxadiazol)-yl]quinuclidine;
3-[5-(3-(4-cyclohexylbutyloxycarbonylamino)-1,2,4-oxadiazol)-yl]quinuclidine;
3-[5-(3-n-butyloxycarbonylamino-1,2,4-oxadiazol)-yl]-1-methyl-1,2,5,6tetrahydropyridine;
3-[5-(3-(2-ethyl-1-butyloxycarbonyl)amino-1,2,4-oxadiazol)-yl]quinuclidine;
3-[5-(3-cyclopentylpropionylamino-1,2,4-oxadiazol)-yl]quinuclidine;
3-[5-(3-hexadecanoylamino-1,2,4-oxadiazol)yl]quinuclidine;
3-[5-(3-cyclohexylacetylamino-1,2,4-oxadiazol)-yl]quinuclidine;
3-[5-(3-isovalerylamino-1,2,4-oxadiazol)yl]quinuclidine;
3-[5-(3-(2-ethylbutyryl)amino-1,2,4-oxadiazol)-yl]quinuclidine;
3-[5-(3-heptyl-4-oxycarbonylamino-1,2,4-oxadiazol)-yl]quinuclidine;
3-[5-(3-(1-ethoxycarbonylprop-2-oxycarbonyl)amino-1,2,4-oxadiazol)-yl]quinuclidine;
3-[5-(3-phenylacetamido-1,2,4-oxadiazol)yl]quinuclidine;
3-[5-(3-cyclohexylcarbonylamino-1,2,4-oxadiazol)-yl]quinuclidine;
3-[5-(3-(2,2-dimethyl)butyrylamino-1,2,4-oxadiazol)-yl]quinuclidine;
3-[5-(3-(2-methoxycarbonyl-2-methyl)propyl-1-oxycarbonylamino-1,2,4-oxadiazol)yl]quinuclidine;
3-[5-(3-n-hexyloxycarbonylamino-1,2,4-oxadiazol)-yl]quinuclidine;
3-[5-(3-n-butyloxycarbonylamino-1,2,4-oxadiazol)-yl]-1,2,5,6-tetrahydropyridine;
3-[5-(3-octanyloxycarbonylamino-1,2,4-oxadiazol)-yl]-1-azabicyclo[2.2.1]heptane;
and salts thereof.

Most of the compounds of this invention have at least one asymmetric centre and often more than one; and can therefore exist as both enantiomers and diastereoisomers. In addition some exist as exo and endo isomers.

It is to be understood that the invention covers all such isomers and mixtures thereof.

Also included within the scope of the present invention are salts of the novel compounds. It will be appreciated that salts of the compounds for use in medicine will be non-toxic pharmaceutically acceptable salts. Other salts may, however, be useful in the preparation of the compounds of the invention or their non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid and phosphoric acid. Where the novel compound carries a carboxylic acid group the invention also contemplates salts thereof, preferably non-toxic pharmaceutically acceptable salts thereof, such as the sodium, potassium and calcium salts thereof.

The method of treatment of this invention includes a method of treating Alzheimer's disease, senile dementia of the Alzheimer type, Huntington's chorea, tardive dyskinesia, hyperkinesia, mania or Tourette syndrome by the administration to a patient in need of such treatment of an effective amount of one or more of the novel compounds.

Moreover, the invention provides in a further aspect a method of treating severe painful conditions (e.g. rheumatism, arthritis and terminal illness) which comprises administering to a patient in need of analgesic treatment an effective amount of one or more of the compounds according to the invention.

This invention therefore also provides a pharmaceutical composition comprising a compound of the invention and a pharmaceutically acceptable carrier.

It may, where appropriate, be advantageous, in order to reduce unwanted peripherally mediated side-effects, to incorporate into the composition a peripherally acting cholinergic antagonist (or anti-muscarinic agent). Thus the compounds of the invention are preferably administered together with a peripheral cholinergic antagonist such as N-methylscopolamine, N-methylatropine, propantheline, methantheline or glycopyrrolate.

The compounds of the invention can be administered orally, parenterally or rectally at a daily dose of about 0.01 to 10 mg/kg of body weight, preferably about 0.1 to 1 mg/kg and may be administered on a regimen of 1-4 times a day. When a cholinergic antagonist is administered, it is incorporated at its conventional dose.

The pharmaceutical formulations of this invention preferably are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like.

The liquid forms in which the novel compositions of the present invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinylpyrrolidone and gelatin.

The compounds of this invention may conveniently be prepared by a process which comprises reacting an oxadiazole substituted on one of the ring carbon atoms thereof with a non-aromatic azacyclic or azabicyclic ring system, and substituted on the other ring carbon atom with amino; with an acylating agent to provide a group which is hydrolysable in vivo to an amino group. The starting materials for this process are obtained by the process described in published European Application No. 239309.

In particular, a compound of formula (III):

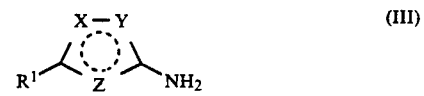

wherein $R^1$, X, Y and Z are as defined with respect to formula (I) above; is reacted with a reactive derivative of a compound which provides the moiety Q of formula CHO, COR or $CO_2R$, where R is an optionally substituted hydrocarbon group.

When the group Q is CHO or COR, the product of the invention is an amide, and the reactive derivative which provides the moiety Q is an N-acylating derivative of formic acid or an acid $RCO_2H$, which may be an acid halide, preferably the acid chloride or bromide, or a symmetrical or mixed anhydride.

Suitable mixed anhydrides are alkoxyformic anhydrides, or anhydrides with, for example, carbonic acid monoesters, trimethylacetic acid, thioacetic acid, diphenylacetic acid, benzoic acid, phosphorus acids (such as phosphoric acid or phosphorous acid) or aliphatic or aromatic sulphonic acids (such as p-toluenesulphonic acid).

Alternative N-acylating derivatives of formic acid or of the acid $RCO_2H$ are the acid azide; activated esters such as esters with 2-mercaptopyridine, cyanomethanol, p-nitrophenol, 2,4-dinitrophenol, thiophenol, halophenols (including pentachlorophenol), monomethoxyphenol, N-hydroxysuccinimide or 8-hydroxyquinoline; amides such as N-acylsaccharins, N-acylthiazoline-2-thione or N-acylphthalimides; or an alkylidene iminoester prepared by reaction of formic acid or of the acid RCO₂H with an oxime.

When the group Q is CO₂R, the product of the invention is a urethane and the reactive derivative which provides the moiety Q is suitably a haloformate, for example a chloroformate ROCOCl prepared from the alcohol ROH and phosgene, COCl₂.

In the process of this invention, any functional groups present in the group R or R¹ may be protected in order to carry out the reaction, and then deprotected thereafter.

For example, hydroxy groups may be protected by means of a silyl group such as a trialkylsilyl group, e.g. trimethylsilyl or t-butyldimethylsilyl. Silyl groups may be removed by aqueous hydrolysis, or preferably with a fluoride.

Suitable carboxyl-protecting derivatives include ester derivatives of the carboxylic acid. Such groups include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, p-toluenesulphonylethyl, methoxymethyl, silyl, stannyl and phosphorus-containing groups.

The carboxylic group or a salt thereof may be regenerated from any of the above esters by conventional methods appropriate to the particular group, for example by acid- or base-catalysed hydrolysis, by treatment with trifluoroacetic acid, by enzymatically-catalysed hydrolysis or by hydrogenation.

Examples of amino-protecting groups include $C_{1-6}$ alkanoyl (for example acetyl, propionyl, n- and isobutyryl and 2,2-dimethylpropanoyl); benzoyl or benzene optionally substituted in the phenyl ring by one or two substituents selected from $C_{1-4}$ alkyl, $C_{1-4}$ alkoxy, trifluoromethyl, halogen and nitro; $C_{1-4}$ alkoxycarbonyl (for example t-butoxycarbonyl); and benzyl optionally substituted as for benzoyl above.

Removal of the amino-protecting group may be effected conventionally, for example by base hydrolysis or by hydrogenolysis.

For the preparation of compounds according to the invention wherein R¹ represents a 1,2,5,6-tetrahydropyridin-3-yl substituent, a pyridine derivative of formula IV:

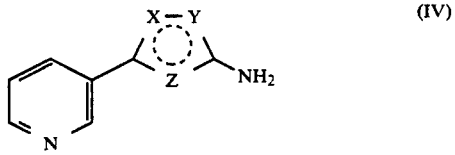

wherein X, Y and Z are as hereinbefore defined; may conveniently be reacted as described above with a reactive derivative of a compound which serves to introduce the moiety Q. Quaternisation of the pyridine ring with, for example, an alkyl halide (e.g. iodomethane) then permits reduction of the pyridinium nucleus of the resulting intermediate (suitably with, for example, sodium borohydride) to yield the required tetrahydropyridine derivative:

The compounds according to the invention are either inactive or behave as muscarinic antagonists in vitro. In vivo, however, they behave as muscarinic agonists, having an activity comparable to that of the compounds described in EP-A-239309. It is believed that this in vivo activity arises as a result of conversion of the compounds according to the invention in vivo into the parent aminooxadiazole compounds. Evidence for this in vivo activity is afforded by the ability of the compounds in question to elicit a mouth movement response (see Salamone et al., Psychopharm., 1986, 88, 467) and/or a hypothermic response, both of which responses are atropine-sensitive. Thus, in these assays the compounds according to the invention were active at doses of 10 mg/kg or less.

The following non-limiting Examples illustrate the preparation of compounds according to the invention.

EXAMPLE 1

3-5-(3-Octanoylamino-1,2,4-oxadiazol)-yl]quinuclidine Hydrogen Oxalate

To a stirred solution of 3-[5-(3-amino-1,2,4-oxadiazol)-yl]quinuclidine (1.00g, 5.15mmol) and 4-dimethylaminopyridine (30mg) in Pyridine (30ml) at 0° was slowly added octanoyl chloride (3.4ml, 0mmol). After 16 hours at 40°, the mixture was evaporated to dryness in vacuo. The residue was dissolved in dichloromethane (30ml), washed with water 2×30ml) then dried (potassium carbonate) and evaporated to dryness in vacuo. The resulting orange oil was Purified by column chromatography on neutral alumina using dichloromethane/methanol (30 : 1) to afford the title compound as a buff coloured solid (0.6g, 36%). The hydrogen oxalate salt had mp 127°–129° C. (methanol/diethyl ether); (Found: C. 56.85; H, 7.46; N, 14.16. $C_{17}H_{28}N_4O_2$. 0.75 $C_2H_2O_4$ requires C, 57.27; H, 7.66; N, 14.44%); $\nu_{max}$ (nujol) 3300–3000 (OH, NH). 2800–2300 NH+) 1720 (C =O, acid); 1630cm⁻¹ (C=O. amide); m/e 320 (M⁺of free base); & (360 MHz, D₂O) 0.84 (3H, t, J =7Hz, CH₃); 1.20–1.40 (8H, m, (CH₂)₄); 1.66–1.72 (2H, m, NHCOCH₂); 80–2.00 and 2 10–2.24 (each 2H, each m. 5 CH₂ and CH₂); 2.51 2H, t, J =7Hz, NHCOCH₂); 2.64–2.68 (1H, m, 4CH); 3.34–3.48 (4H, m, 6CH₂ and 7CH₂) and 3.76–3.92 (3H, m, 2CH₂ and 3CH).

EXAMPLE 2

3-5-(3-Benzoylamino-1,2,4-oxadiazol)-yl]quinuclidine Hydrogen Oxalate

The title compound free base was obtained (0.22g. 14%) from 3-[5-(3-amino-1,2,4-oxadiazol)-yl]quinuclidine (1.00g, 5.15mmol) and benzoyl chloride (2.4ml, 20mmol) in the same manner as described for Example 1. The hydrogen oxalate salt had mp 122°–125° C.; (Found: C, 52.15; H, 4.85; N, 13.18. $C_{16}H_{18}N_4O_2$. 1.5 $C_2H_2O_4$. 0.1 H₂O requires C. 52.43; H, 4.91; N, 12.87%); $\nu_{max}$ (nujol) 3700–3000(OH, NH), 2800–2300 (NH+), 1710 (C =O, acid), 1625 cm⁻¹ (C=O, amide); m/e 301 (CI⁺, [M +H]⁺ of free base reduction product); δ (360 MHz, D₂O) 1.90–1.98 and 2.06–2.20 (each 2H, each m, 5CH₂ and 8CH₂); 2.60–2.64 and 2.70–2.74 (1H, each m, 4CH, E/Z rotamers); 3.28–3.52 (6H, m, 2CH, 3CH, 6CH₂ and 7CH₂); 3.80–3.96 (1H, m, 2CH); 7.56–7.66 (2H, m, ArH); 7.69–7.76 (1H, m, ArH); 7.93 and 8.13 (1H, each dd, J =1 and 9Hz, ArH, E/Z rotamers).

EXAMPLE 3

3-5-(3-Isobutyrylamino-1,2,4-oxadiazol)-yl]quinuclidine Hydrogen Oxalate

The free base of the title compound was obtained (0.15g, 14%) from 3-[5-(3-amino-1,2,4-oxadiazol)-yl]quinuclidine (0.80g, 4.12mmol) and isobutyryl chloride (2.1 ml, 20mmol) in a manner similar to that described for Example 1, except that the reaction mixture was heated at 40° for 2 days. The hydrogen oxalate salt had mp 144°-145° C. (methanol/diethyl ether); (Found: C, 48.35; H. 5.86; N, 14.26. $C_{13}H_{20}N_4O_2$. 1.5 $C_2H_2O_4$ requires C, 48.12: H, 5.80; N, 14.03%): $\nu_{max}$ (nujol) 3300-3100 (OH, NH), 2800-2400 (NH+) 1720 (C =O, acid), 1640 cm$^{-1}$ (C =O, amide); m/e 267 (CI+, [M H]+ of free base reduction Product); δ (360 MHz, $D_2O$) 1.19 (6H, d, J =7Hz, 2 ×$CH_3$); 1.8-2.0 and 2.02-2.22 (each 2H, each m, 5$CH_2$ and 8$CH_2$); 2.60-2.66 (1H, m, 4CH); 2.70-2.82 (1H, m, COCH); 3.26-3.50 (4H, m, 6$CH_2$ and 7$CH_2$); 3.72-3.92 (3H, m, 2CH and 3CH).

EXAMPLE 4

3-[5-(3-(2,2-Dimethylpropionyl)amino-1,2,4-oxadiazol-)yl]quinuclidine Hydrogen Oxalate The title compound free base was obtained (0.25g, 22%) from 3-[5-(3-amino-1,2,4-oxadiazol)-yl]quinuclidine (0.8q. 4.12mmol) and 2.2-dimethyl propionyl chloride (2.5ml. 20mmol) in a manner similar to that described for Example 1 except that the reaction mixture was heated at 40° for 3 days. The hydrogen oxalate salt had mp >125° C. (dec) (dichloromethane/diethyl ether): (Found: C. 50.82: H, 7 07; N, 12.92. $C_{14}H_{22}N_4O_2$. 1.5 $C_2H_2O_4$. 0.5 ($CH_3CH_2$)$_2$O requires C, 50.66 H, 6.71, N, 12.45%); $\nu_{max}$ (nujol) 3700-3000 (OH. NH), 2800-2300 (NH+), 1710 (C =O, acid), 1640 cm$^{-1}$ C =O. amide); m/e 279 (FAB+, [M +H]+ of free base); δ (360 MHz, $D_2O$) 1.41 (9H, s, 3 ×$CH_3$); 1.86-1.94 and 2.06-2.13 (each 2H, each m, 5$CH_2$ and 8$CH_2$); 2.54-2.60 (1H, m, 4CH); 3.26-3.48 (6H, m, 2CH, 3CH, 6$CH_2$ and 7$CH_2$); 3.82 (1H.,dd, J=5 and 14Hz, 2CH).

EXAMPLE 5

3-[5-(3-Ethoxycarbonylamino-1,2,4-oxadiazol)-yl]quinuclidine

To a solution of 3-[5-(3-amino-1,2,4-oxadiazol)yl]-quinuclidine (1.00g. 5.15mmol) and 4-dimethylaminopyridine (30mg) in Pyridine (30ml) stirred at 0° was added ethylchloroformate (1.96ml. 20.6mmol) dropwise. The reaction mixture was stirred at 40° for 16 hours then evaporated in vacuo. The residue was partitioned between dichloromethane (30ml) and water (30ml) containing Potassium carbonate (2q). The organic layer was separated and the aqueous re-extracted with dichloromethane (2 x 30ml). The combined organic extracts were washed with water (30ml), dried (Potassium carbonate) then evaporated. The resulting brown solid was Purified by column chromatography on neutral alumina using dichloromethane/methanol (30 : 1 to afford the title compound as a colourless solid (0.48g, 36%) of mp 169°-170° C.: (Found: C. 53.87; H, 6.63: N, 20.75. $C_{12}H_{18}N_4O_3$ requires C, 54.12: H, 6.81; N, 21.04%) $\nu_{max}$ nujol) 2700-2500 (NH), 1740 cm$^{-1}$ C=O); m/e 266 +); δ (360MHz, $CDCl_3$) 1.32 (3H, t, J =7Hz. $CH_2CH_3$); 1.42-1.46 and 1.76-1.82 (each 2H, each m, 5$CH_2$ and 8$CH_2$); 2.30-2.34 (1H, m, 4CH); 2.72-2.80 (1H, m, ·6CH); 2.90-3.02 (2H, m, 7$CH_2$); 3.08-3.20 (3H, m, 2CH, 3CH and 6CH); 4.04 (1H, d, J =11Hz, 2CH); 4.24 (2H, q, J =7Hz, $CH_2CH_3$); 11.87 (1H, broad s, NH).

EXAMPLE 6

3-[5-(3-iso-Propyloxycarbonylamino-1,2,4-oxadiazol)-yl]quinuclidine Hydrochloride To a stirred suspension of 3-[5-(3-amino-1,2,4-oxadiazol)-yl]quinuclidine (0.75g, 3.86mmol) in dry dichloromethane (25ml) at 0° was added triethylamine (0.54ml, 3.9mmol) followed by iso-Propylchloroformate (4.4ml, 39mmol) dropwise. After 1 hour at 0° followed by 24 hours at room temperature, further iso-Propylchloroformate (2.2ml, 19mmol) was added. After 24 hours at room temperature the mixture was evaporated to dryness in vacuo and the residue in dichloromethane (30ml) washed with water 30ml) containing potassium carbonate (2g). The organic layer was separated and the aqueous re-extracted with dichloromethane (30ml). The material isolated from the combined organic extracts was purified by column chromatography on neutral alumina to afford the title compound free base as a Pale yellow solid (0.41g, 38%), mp 170°-172° C. The hydrochloride salt had mp 106°-108° C.; (Found: C 46.57; H, 6.87; N, 16.75. $C_{13}H_{20}N_4O_3$. HCl. $H_2O$ requires C, 46.64; H, 6.92; N, 16.73%); $\nu_{max}$ (nujol) 3700-3000 (NH, OH), 2800-2400 (NH+), 1735 C =O); m/e 280 (M+ of free base); δ (360 MHz, $D_2O$) 1.32 (6H, d, J = 6Hz, 2 ×$CH_3$); 1.84-2.00 and 2.10-2.22 (each 2H, each m, 5$CH_2$ and 8$CH_2$); 2.65-2.68 (1H, m, 4CH); 3.38-3.50 (4H, m, 6$CH_2$ and 7$CH_2$); 3.78-3.92 (3H, m, 2$CH_2$ and 3CH); 5.02 (1H, septet, J =6Hz, CH($CH_3$)$_2$).

EXAMPLE 7

3-[5-(3-t-Butyloxycarbonylamino-1,2,4-oxadiazol)-yl]quinuclidine Hydrochloride To a stirred solution of 3-[5-(3-amino-1,2,4-oxadiazol)-yl]quinuclidine (1.00g. 5.15mmol) and 4-dimethylaminopyridine (30mg) in Pyridine (30ml) at 0° was added di-t-butyldicarbonate (1.62g, 12mmol). After 1 hour at ° followed by 24 hours at room temperature, the mixture was evaporated in vacuo and the residue Partitioned between dichloromethane (30ml) and water (30ml) containing Potassium carbonate (2g). The organic layer was separated and the aqueous re-extracted with dichloromethane 30ml). The material isolated from the combined organic extracts was Purified by column chromatography on neutral alumina using dichloromethane/ methanol (30 : 1) to give the guinuclidine free base as a Pale yellow solid (0.60g, 40%). The hydrochloride salt had mp 130°-132° C. (propan-2-ol/diethyl ether): (Found: C, 50.64; H, 7.58: N, 13.93. $C_{14}H_{22}N_4O_3$. HCl. 0.9 ($CH_3$)$_2$CHOH. 0.5$H_2O$ requires C, 50.91; H, 7.98; N, 14.22%); $\nu_{max}$ (nujol) 2800-2400 (NH, NH ), 1730 (C =O); m/e 293 (FAB-, [M-H]- of free base); δ (360MHz, $D_2O$) 1.53 (9H, s, 3 ×$CH_3$); 1.86-1.98 and 2.12-2.20 (each 2H, each m, 5$CH_2$ and 8$CH_2$); 2.66-2.68 (1H. m, 4CH); 3.38-3.48 4H, m, 6$CH_2$ and 7CH ); 3.78-3.90 (3H, m, 2CH and 3CH).

EXAMPLE 8

3-5-(3-iso-Butyloxycarbonylamino-1,2 4-oxadiazol)-yl]quinuclidine Hydrochloride The title compound free base was obtained (1.32q 87%) from 3-[5-(3-amino-1,2,4-oxadiazol)-yl]quinuclidine (1.00g, 5.15mmol) and iso-butyl chloroformate (6.5ml, 50mmol) as given in Example 5, except that the reaction was stirred at 8° for 36 hours. The hydrochloride salt had mp 85°–87° C. (dichloromethane/diethyl ether); (Found: C, 49.09; H, 6.91; N, 16.51. $C_{14}H_{22}N_4O_3$. HCl. $0.5H_2O$ requires C, 49.48; H, 7.10; N, 16.49%); $\nu_{max}$ (nujol) 3700–3100 (NH, OH), 2800–2300 (NH+). 1735 C=O); m/e 294 (M+ of free base); δ (360MHz, $D_2O$) 0.94 (6H, d, J=6.5Hz, 2 ×$CH_3$); 1.84–2.00 and 2.12–2.22 (each 2H, each m, 5$CH_2$ and 8$CH_2$); 1.99 (1H, tg. J=6.5 Hz, $CH_2CH(CH_3)_2$); 2.65–2.68 (1H, m, 4CH); 3.33–3.50 (4H, m, 6$CH_2$ and 7$CH_2$); 3.75–3.90 (3H, m, 2$CH_2$ and 3CH); 4.02 (2H, d, J =6.5Hz, O$CH_2$CH).

EXAMPLE 9

3-[5-(3-(9-Fluorenyl)methyloxycarbonylamino-1,2,4-oxadiazol)-yl[quinuclidine Hydrochloride The title compound free base was obtained (0.37g, 18%) from 3-[5-(3-amino-1,2,4-oxadiazol)-yl]quinuclidine (1.00q. 5.15mmol) and 9-fluorenylmethylchloroformate (2.66g, 10.3mmol) as described in Example 5, except that the reaction was stirred at room temperature for 18 hours. The hydrochloride salt had mp 129°–132° C.; (Found: C, 63.83; H, 5.72; N, 11.11. $C_{24}H_{24}N_4O_3$. HCl requires C, 63.64; H, 5.56; N, 12.37%); m/e 417 (FAB+, [M +H]+ of free base); δ (360 MHz, $D_2O$) 1.40–1.75 and 1.80–2.04 (each 2H, each m, 5$CH_2$ and 8$CH_2$) : 2.24–3.32 (1H, m, 4CH); 3.20–3.60 (4H, m,·6$CH_2$ and 7$CH_2$); 3.6–3.9 (3H, m, 2$CH_2$ and 3CH); 3.88–4.00 (1H. m, $CH_2$CH); 4.04–4.28 (2H, m, $CH_2$CH); 6.92–7.14 (4H, m, ArH); 7.28–7.46 (4H, m, ArH).

EXAMPLE 10

3-[5-(3-Cyclohexylmethoxycarbonylamino-1,2,4-oxadiazol) -yl] quinuclidine Hydrochloride To a solution of cyclohexylmethanol (5.5ml, 43.8mmol) in dry toluene (5ml) at 0° C. was added dropwise a solution of Phosgene in toluene (21.5ml, 1.93M, 41.5mmol). The solution was stirred at 0° C. for 1 hour then added dropwise to a stirred solution of 3-[5-(3-amino-1,2,4-oxadiazol)-yl]quinuclidine (860mg, 4.4mmol) in Pyridine (30ml), containing 4-dimethylaminopyridine (20mg) at 0° C. The solution was allowed to warm slowly to 20° C. then stirred for 16 hours. The solvent was removed under reduced pressure, saturated $K_2CO_3$ solution (40ml) was added to the residue and then extracted with dichloromethane (3×40ml). The combined extracts were dried ($Na_2SO_4$), concentrated under reduced pressure, and the crude Product chromatographed on rade III neutral alumina eluting with a radient of MeOH/$CH_2Cl_2$ to give a solid which was crystallised from MeOH/diethyl ether. The Pure Product was dissolved in dichloromethane and treated with ethereal HCl to give, after recrystallisation from MeOH/diethyl ether, the title compound, mp 226° C. 794mg); Found: C, 54.77: H, 7.30; N, 15.03; Cl, 9.68. $C_{17}H_{26}N_4O_3$ HCl requires C, 55.05; H, 7.34; N, 15.11; Cl. 9.56%): $\nu_{max}$ (nujol) 1760cm$^{-1}$ (C=O); m/e 335 (FAB+, [M +H]+ of free base); δ (360MHz, $D_2O$) 1.0–1.3 (5H, m. cyclohexyl $CH_2$ axial), 1.6–1.8 (6H, m, cyclohexyl CH equatorial and O$CH_2$CH), 1.82–2.00 and 2.10–2.25 (each 2H, each m, 5$CH_2$ and 8$CH_2$ ), 2.64–2.68 (1H, m, 4CH); 3.35–3.50 (4H, m, 5$CH_2$ and 7$CH_2$); 3.76–3.92 (3H, m, 2$CH_2$ and 3CH) and 4.07 (2H, d, J =6Hz, O$CH_2$).

EXAMPLE 11

3-[5-(3-(2,2-Dimethylpropyl-1-oxycarbonylamino)-1,2,4-oxadiazol)-yl quinuclidine Hydrochloride.

The title compound free base was obtained (0.52g, 4%) from 3-[5-(3-amino-1,2,4-oxadiazol)-yl]quinuclidine (0.75q, 3.86mmol), phosgene 19.2ml of a 0% solution in toluene, 39mmol) and neo-pentyl alcohol (3.44g, 39mmol) following the Procedure given in Example 10. The hydrochloride salt had mp 212°–214° C.; (Found: C, 50.71: H, 7.39; N, 15.77%. $C_{15}H_{24}N_4O_3$. HCl. $0.5H_2O$ requires C, 50.92; H, 7.41; N, 15.83%): $\nu_{max}$ (nujol) 3600–3000 (OH, NH), 2800–2300 (NH+), 1740cm$^{-1}$ (C =O); m/e 308 (M+ of free base): δ (360 MHz, $D_2O$) 0.96 (9H, s, 3 ×$CH_3$; 1.86–2.00 and 2.14–2.22 (each 2H, each m, 5$CH_2$ and 8$CH_2$); 2.66–2.69 (1H, m, 4CH); 3.36–3.52 (4H, m, 6$CH_2$ and 7$CH_2$); 3.78–3.92 (3H, m, 2$CH_2$ and 3CH); 3.96 (2H, s, $CH_2$).

EXAMPLE 12

3-[5-(3-Cyclohexyloxycarbonylamino-1,2,4-oxadiazol)-yl ]quinuclidine Hydrochloride The title compound free base was obtained (0.67g, 55%) from 3-[5-(3-amino-1,2,4-oxadiazol)-yl]quinuclidine (0.75q. 3.S6mmol). phosgene (19.2ml of a 20% solution in toluene. 39mmol) and cyclohexanol (4.1ml, 39mmol) as described in Example 10. The hydrochloride salt had mp 199°–201° C. (dichloromethane/diethyl ether); (Found: C, 52.80; H, 7 08; N, 15.20. $C_{16}H_{24}N_4O_3$. HCl $0.5H_2O$ requires C, 52.53; H, 7.16; N, 15.31%); $\nu_{max}$ (nujol) 3600–3100 (NH, OH), 2700–2350 (NH+). 1740cm$^{-1}$ (C=O); m/e 320 (M of free base); δ (360MHz, $D_2O$) 1.24–1.50 and 1.50–1.62 (each 3H, each m, cyclohexyl-H); 1.68–1.80 (2H, m, cyclohexyl-H); 1.84–2.00 4H, m, cyclohexyl-H, 5CH and 8CH); 2.16 (2H, dm, J =9Hz, 5CH and 8CH); 2.66–2.69 (1H, m, 4CH); 3.34–3.50 (4H, m, 6$CH_2$ and 7$CH_2$); 3.75–3.93 (3H, m, 2$CH_2$ and 3CH); 4.75–4.80 (1H, m, OCH).

EXAMPLE 13

3-[5-(3-Octanyloxycarbonylamino-1,2,4-oxadiazol)-yl quinuclidine Hydrochloride

This was prepared from 3-[5-(3-amino-1,2,4-oxadiazol)-yl]quinuclidine (0.75g, 3.86mmol), phosgene (19.2ml of a 20% solution in toluene, 39mmol) and 1-n-octanol (6.1ml. 39mmol) as described in Example 10 (0.75g, 55%). The hydrochloride salt had mp 95°–96° C. (dichloromethane/diethyl ether); (Found: C, 54.89; H, 8.05; N, 14.29. $C_{18}H_{30}N_4O_3$. HCl. $0.5H_2O$ requires C, 4.60; H, 8.15; N, 14.15%): $\nu_{max}$ (nujol) 0 3600–3400 (OH), 3400–3100 (NH). 2800–2200 (NH+), 720cm$^{-1}$ (C=O); m/e 351 (CI+, [M +H]+ of free base); δ (360MHz, $D_2O$) 0.86 (3H, t, J =7Hz, $CH_3$); 1.20–1.45 (10H, m, ($CH_2)_5CH_3$); 1.68–1.75 (2H, m, COO$CH_2$$CH_2$); 1.83–2.00 and 2.12–2.23 (each 2H, each m, 5$CH_2$ and 8$CH_2$); 2.65–2.68 (1H, m, 4CH); 3.35–3.50 (4H, m, 6$CH_2$ and 7$CH_2$); 3.78–3.94 (3H, m, 2$CH_2$ and 3CH); 4.25 (2H, t, J =6.5 Hz, COO$C_2$$CH_2$).

EXAMPLE 14

DL-3-[5-(3-(1-(3-n-Pentyloxycarbonyl)-1-ethyloxy-carbonylamino)-1,2,4-oxadiazol)-yl]quinuclidine Hydrochloride.

Using the method described in Example 17, the title compound free base was obtained (0.70g. 38%) from 3-[5-(3-amino-1,2,4-oxadiazol)-yl]quinuclidine (1.00g, 5.1mmol), Phosgene (23ml of a 20% solution in toluene. 48mmol) and 3-n-pentanyl-DL-lactic acid ester (7.8g of crude material; prepared by heating DL-lactic acid (8g, 89mmol) with 3-n-Pentanol (17.6g, 200mmol) and concentrated sulphuric acid (0.3ml) under reflux for 16 hours). The hydrochloride salt had mp 103°-110° C. (dichloromethane/diethyl ether); (Found: C, 51.07; H, 7.23; N, 13.49. $C_{18}H_{28}N_4O_5$ HCl 0.5$H_2O$ requires C. 50.76; H, 7.10; N, 13.16%); $v_{max}$(nujol) 3700-3100 (OH, NH), 2800-2300 (NH+), 1740cm$^{-1}$ (C =O); m/e 380 (M+ of free base); δ (360 MHz. $D_2O$) 0.84 and 0.88 (6H. each t, J =7.5Hz, 2 ×$CH_2CH_3$, diastereomer ratio 1 : 1); 1.58 (3H, d, J =7Hz, OCHCH$_3$); 1.55-1.70 (4H, m. 2 ×$CH_2CH_3$); 1.82-2.00 and 2.10-2.23 (each 2H, each m, 5$CH_2$ and 8$CH_2$); 2.64-2.68 (1H, m. 4CH); 3.34-3.50 (4H, m, 6$CH_2$ and 7$CH_2$); 3.76-3.93 (3H, m, 2$CH_2$ and 3CH): 4.80-4.90 (1H, m, OCHCH$_2$CH$_3$); 5.16 (1H, q, J =7Hz, OCHCH$_3$).

EXAMPLE 15

3-[5-(3-(3-Phenylpropyl-1-oxycarbonylamino)-1,2,4-oxadiazol)-yl]quinuclidine Hydrochloride.

This was prepared exactly as described in Example 10 but using 3-Phenylpropanol in place of cyclohexylmethanol. The compound had mp 188°-190° C. ($CH_2Cl_2$/$Et_2O$); (Found: C, 55.74; H, 6.55; N, 13.66. $C_{19}H_{24}N_4O_3$. HCl. $H_2O$ requires C. 55.79; H. 6.62; N, 13.64%); $v_{max}$($CH_2Cl_2$) 1760cm$^{-1}$(C=O); m/e 356 (M of free base); δ (360 MHz, $D_2O$) 1.80-2.00 and 2.10-2.24 (each 2H, each m, 5$CH_2$ and 8$CH_2$), 2.06 (2H, quintet, J =7 Hz, OCH$_2$CH$_2$) 2.64-2.70 (1H. m, 4CH), 2.77 (2H, t, J =7HZ, CH$_2$ph). 3.34-3.50 (4H, m. 6$CH_2$ and 7$CH_2$), 3.75-3.90 (3H, m, 2$CH_2$ and 3CH), 4.26 (2H, t, J =7Hz, O$CH_2$) and 7.20-7.40 (5H, m, Ph).

EXAMPLE 16

3-[5-(3,3-Dimethylbutyl-1-oxycarbonylamino)-1,2,4-oxadiazol)-yl]quinuclidine Hydrochloride.

The title compound was prepared from 3,3-dimethylbutanol exactly as described in Example 10 and had mp 177° C. (free base) ($CH_2Cl_2$/$Et_2O$); (Found: C, 52.71; H, 7.64; N, 15.54; Cl, 9.87. $C_{16}H_{26}N_4O_3$. HCl. 0.25 $H_2O$ requires C, 52 89; H, 7.63; N, 15.42; Cl, 9.76%); $v_{max}$ ($CH_2Cl_2$) 1760cm$^{-1}$ (C =O); m/e 323 (FAB+, [M +H]+ free base); δ (360MHz, $D_2O$) 0.84 (9H, s, (CH$_3$); 1.53 (2H, t, J=7.2Hz, OCH$_2$CH$_2$), 1.70-1.89 and 1.97-2.13 (each 2H, each m, 5$CH_2$ and 8$CH_2$), 2.53-2.58 (1H, m, 4CH), 3.22-3.40 (4H, m, 6$CH_2$ and 7$CH_2$). 3.65-3.82 (3H, m, 2$CH_2$ and 3CH) and 4.22 (2H, t, J =7.2Hz, O$CH_2$).

EXAMPLE 17

3-[5-(3-Pent-3-oxycarbonylamino-1,2,4-oxadiazol)-yl]quinuclidine Hydrogen Oxalate.

To a solution of pentan-3-ol (4.76ml, 13.9mmol) in toluene (5ml) cooled to −20° C. was added dropwise phosgene in toluene (21.5ml, 1.93M, 41.5mmol). The solution was stirred at −20° C. for 2 hours then a solution of 3-[5-(3-amino-1,2,4-oxadiazol)-yl]quinuclidine (860mg, 4.4mmol) in Pyridine (30ml). containing 4-dimethylaminopyridine (20mg), was added dropwise. The reaction was stirred at −20° C. for 2 hours then allowed to warm slowly to 20° C. and stirred at this temperature for 12 hours. The reaction mixture was concentrated in vacuo and the residue in $K_2CO_3$ solution (50ml) was extracted with $CH_2Cl_2$ (3×50 ml). The combined extracts were dried ($Na_2SO_4$) and concentrated under reduced Pressure to give a residue which was Purified by chromatography on grade III neutral alumina eluting with MeOH/$CH_2Cl_2$ (1 : 99). The Product thus obtained was further Purified as the oxalate salt, mp 70°-73° C. (MeOH/$Et_2O$); (Found: C, 45.61; H, 5.94; N, 11.34. $C_{15}H_{24}N_4O_3$.2(COOH)$_2$ 0.75 $H_2O$ requires C, 45.46; H, 5.92; N, 11.16%); $v_{max}$ (nujol) 1645cm$^{-1}$ (C=O) on free base; m/e 307 (CI−, (M−H)− of free base); δ (360MHz, $D_2O$) 0.90 6H, t, J =7.5H, 2 ×$CH_3$), 1.58-1.71 (4H, m, 2 ×$CH_2CH_3$), 1.80-1.9B and 2.06-2.20 (each 2U, each m, 5$CH_2$ and 8$CH_2$), 2.63-2.68 (1H, m, 4CU), 3.32-3.48 (4H, m, 6CH and 7CH ), 3.74-3.90 (3H, m, 2$CH_2$ and 3CH) and 4.70-4.78 (1H, m, OCH).

EXAMPLE 18

3-[5-(3-(2-Propylpentyl-1-oxycarbonylamino)-1,2,4-oxadiazol)-yl]quinuclidine Hydrogen Oxalate This was Prepared in a similar manner to that described in Example 17 using 2-Propylpentan-1-ol and obtained as white crystals, mp 122° C. (Propan-2-ol/$Et_2O$) (Found: C, 54.80; H. 7.26; N, 12.84. $C_{18}H_{30}N_4O_3$.(COOH)$_2$ requires C, 54.53; H, 7.32; N, 12.72%); $v_{max}$ (nujol) 1750cm$^{-1}$ (C=O); m/e 351 (CI+), [M+H]+ of free base); δ (360MHz. $D_2O$) 0.80-0.96 (6H, m, 2 ×CH$_3$) 1.24-1.40 (8H, m, 2 ×$CH_2CH_2CH_3$), 1.70-1.80 (1H, m, O$CH_2$CH). 1.80-2.00 and 2.08-2.23 (each 2H, each m, 5$CH_2$ and 8$CH_2$), 2.62-2.66 (1H, m, 4CH), 3 33-3.51 (4H, m, 6$CH_2$ and 7$CH_2$), 3.76-3.92 (3H, m, 2$CH_2$ and 3CH) and 4.15 (2H, d, J =5.6Hz, O$CH_2$).

EXAMPLE 19

3-[5-(3-Acetamido-1,2,4-oxadiazol)-yl]quinuclidine

3-[5-(3-Amino-1 2.4-oxadiazol)-yl]quinuclidine (1.75g, 9.0mmol) was heated under reflux in a mixture (1 : 1) of acetic acid and acetic anhydride (35ml). The reaction was cooled and concentrated under reduced Pressure. The residue was dissolved in water (50ml). adjusted to PH10 with $K_2CO_3$, and extracted with dichloromethane (4×50ml). The combined extracts were dried and concentrated under reduced Pressure and the residue chromatographed on grade III neutral alumina eluting with MeOH/$CH_2Cl_2$ (3 : 97). The title product thus obtained was further Purified by recrystallisation from $CH_2Cl_2$/$Et_2O$, mp 192°-193° C. (320mg); (Found: C, 55.89; H, 6.83; N, 6.87. $C_{11}H_{16}N_4O_2$ requires C, 55.92; H, 6.83; N, 6.71%); $v_{max}$ (nujol) 1715cm$^{-1}$ (C =O): m/e 236 (M+)δ 360MHz, CDCl$_3$) 1.44-1.53 and 1.78-1.86 (each 2H, each m, 5$CH_2$ and 8$CH_2$). 2.20 (3H, bs, CH$_3$), 2.29-2.36 (1H, m, 4CH), 2.75-2.85, 2.98-3.06 and 3 12-3.28 (each 2H, each m, 2$CH_2$). 6$CH_2$ and 7$CH_2$) and 4.00-4.18 (1H, m, 3CH).

EXAMPLE 20

3-[5-(3-Formamido-1 2 4-oxadiazol)-yl]quinuclidine

3-[5-(3-Amino-1,2,4-oxadiazol)-yl]quinuclidine (800mg, 4.1mmol) was stirred with formic acetic anhydride (10ml) at 0° C. for 2 hours. The reaction was concentrated under reduced pressure and the residue dissolved in water (30ml) to which aqueous $K_2CO_3$ solution was added until PH 10 The solution extracted with dichloromethane (4×30ml) and the combined extracts dried ($Na_2SO_4$) and concentrated in vacuo. The title compound was obtained pure by crystallisation of the residue from $CH_2Cl_2$/$Et_2O$, mp. 147°-148° C.

(350mg); (Found: C, 54.07; H, 6.26: N, 25.11. $C_{10}H_{14}N_4O_2$ requires C, 54.04; H, 6.35; N, 25.21%); m/e 222 (M+); δ (360MHz, $D_2O$) 1.44-1.56 and 1.76-1.86 (each 2H, each m, $5CH_2$ and $8CH_2$). 2.28-2.36 (1H, m, 4CH), 2.78-3.16 (6H, m, $2CH_2$. $6CH_2$ and $7CH_2$). 3.77-3.88 (1H, m, 3CH) and 9.05 (1H, s. NCHO).

EXAMPLE 21

3-[5-(3-Butyloxycarbonylamino-1,2,4-oxadiazol)-yl]quinuclidine Hydrochloride

The title compound free base was obtained (1.76g, 54%) from 3-[5-(3-amino-1,2,4-oxadiazol)-yl]quinuclidine (2.1g, 11mmol) and n-butylchloroformate (14ml, 110mmol) as given in Example 5, except that the reaction was stirred at 4° C. for 16 hours. The hydrochloride salt had mp 99.5°-101.5° C. (dec); (Found: C, 48.42; H, 6.66; N, 16.08. $C_{14}H_{22}N_4O_3$ 1.5 HCl requires C, 48.18; H, 6.79: N, 16.05%); δ (360MHz, $D_2O$) 0.92 (3H, t, J=7Hz, $CH_3$); 1.39 (2H, sextet, J =7Hz, $C_2CH_3$); 1.69 (2H, quintet, J=7Hz, CO ); 1.86-1.94 (2H, m) and 2.12-2.17 (2H, m, $5\text{-}CH_2$ and $8\text{-}CH_2$); 2.65 (1H, q, J=3Hz, 4-CH); 3.34-3.49 (4H, m) and 3.76-3.87 (3H, m, $2\text{-}CH_2$, 3-CH, $6\text{-}CH_2$ and $7\text{-}CH_2$); 4.24 (2H, t, J =7Hz, $COOCH_2$).

EXAMPLE 22

3-5-(3-(4-Methyl-1-pentanyloxycarbonylamino)1,2,4-oxadiazol)-yl]quinuclidine Hydrochloride This was prepared from 3-[5-(3-amino-1,2,4-oxadiazol)-yl]quinuclidine (0.75g, 3.86mmol), phosgene (24ml of a 20% solution in toluene, 49mmol) and 4-methyl-1-Pentanol (5.0g, 49mmol) as described in Example 10 and had mp 55°-57° C. (dichloromethane/diethyl ether); (Found: C, 52.64; H, 7.51; N, 14.80. $C_{16}H_{26}N_4O_3$. HCl. $0.5H_2O$ requires C, 52.28; H, 7.67; N, 15.22%); $v_{max}$ (nujol) 3700-3100 (OH and NH), 2700-2300 (NH+), 1735 (C=O); m/e 322 (M+ of free base); δ (360MHz, $D_2O$) 0.88 (6H, d, J=6 5Hz, $CH(CH_3)_2$) 1.22-1.30 2H, m, $CH_2CH$): 1.58 (1H, tq, J =6.5Hz, $CH_2CH$); 1.67-1.75 (2H, m, $CH_2CH_2CH_2CH$); 1 1.80-2.02 and 2.10-2.22 (each 2H. each m, $5CH_2$ and $8CH_2$); 2.65-2.68 (1H, m, 4CH); 3.32-3.50 (4H, m) and 3.76-3.90 (3H, m, $2CH_2$, 3CH, $6CH_2$ and $7CH_2$); 4.23 (2H. t, J =6.5Hz, $COOCH_2CH_2$).

EXAMPLE 23

3-[5-(3-(4-Cyclohexylbutyloxycarbonylamino)-1,2,4-oxadiazol)-yl]quinuclidine Hydrogen Oxalate This was prepared from 3-[5-(3-amino-1,2,4phosgene (15ml of 20% solution in toluene, 30mmol) and 4-cyclohexylbutanol (4.75g, 30mmol) as described in Example 10 and had mp 135°-137° C. (methanol/diethyl ether); (Found: C, 56.51; H, 7.46; N, 12.09. $C_{20}H_{32}N_4O_3$. $C_2H_2O_4$ requires C. 56.64; H, 7.35; N, 12.01%); m/e 377 FAB+, M+H+ of free base); δ (360MHz, $D_2O$) 0.76-0.98 (2H. m, cyclohexyl-$CH_2$); 1.06-1.42 and 1.56-1.84 (15H, m, 4×cyclohexyl-$CH_2$, cyclohexyl-CH and $COOCH_2$ $(CH_2)_3$); 1.88-2.02 (1H, m) and 2.04-2.26 (3H, m. $5CH_2$ and $8CH_2$): 2.56-3.02 (1H m. 4CH): 3 34-3.50 (4H. m) and 3.76-3.94 (3H m. $2CH_2$, 3CH. 6CH and $7CH_2$); 4 16 (2H, t, J =7Hz, $COOCH_2$)

EXAMPLE 24

3-[5-(3-n-Butyloxycarbonylamino-1,2,4-oxadiazol)yl]-1-methyl-1,2,5,6-tetrahydropyridine Hydrogen Oxalate.

a) 3-[5-(3-Amino-1,2,4-oxadiazol)-yl]pyridine

A suspension of hydroxyguanidine sulphate (97.2g, 0.37mol) was stirred with 4A molecular sieves (70g) in ethanol (450ml) under a nitrogen atmosphere for 2 hours. Sodium (16.8g, 0.73mol) was added in small Portions over 45 minutes. After 2 hours a solution of methyl nicotinate (10.0g, 0.073mol) in ethanol (150ml) was added and the reaction mixture was stirred whilst heating under reflux for 4 hours. The reaction mixture was cooled, filtered then evaporated to dryness and the residue was partitioned between water (200ml) and dichloromethane (200ml). The organic layer was separated and the aqueous further extracted with dichloromethane (200ml) then ethyl acetate (3 x 200ml). The organic fractions were dried (sodium sulphate) then evaporated to dryness to give a yellow solid (3.1g). Recrystallisation from methanol/ethyl acetate 1:10) gave the title product as a cream crystalline solid (2.08g, 18%); $R_f$=0.45 in ethyl acetate on silica; mp 188°-190° C. (Found: C, 51.53; H, 3.80; N, 34.30; C requires C, 51.85; H, 3.73; N, 34.55%); $v_{max}$ (nujol) 3400, 3320, 3170 $cm^{-1}$ (NH), 1650, 1635, 1610$cm^{-1}$ (C=C, C=N); δ (360MHz, d6DMSO) 6.51 (2H, s, $NH_2$); 7.63 (1H, dd, J =5, 8Hz, 5-CH); 8.34 (1H, dt, J=2.8Hz, 4-CH); 8.82 (1H, dd, J=2,5 Hz, 6-CH); 9.14 (1H, d, J =2Hz, 2-CH).

b) 3-[5-(3-n-Butyloxycarbonylamino-1,2,4-oxadiazol)-yl]pyridine

To a stirred, cooled (0° C.) suspension of 3- 5-(3-amino-1,2,4-oxadiazol)yl]pyridine (0.75g, 0.0046mol) in pyridine (25ml) was added 4-dimethylaminopyridine (10mg) followed by dropwise addition of n-butylchloroformate (5 8ml, 0.046mol). After 1 hour at 0° C. the reaction mixture was stirred at room temperature for 24 hours, then evaporated to dryness. The residue was dissolved in dichloromethane (100ml) then washed with water (2×50ml). dried (sodium sulphate) then evaporated to dryness to give a yellow semisolid which was Purified by column chromatography on silica by elution with dichloromethane/methanol (100:1).

3-[5-(3-(Di-n-butyloxycarbonyl)amino-1,2,4-oxadiazol)-yl]Pyridine (0.50g) was isolated as a pale yellow oil; $R_f$=0.55 in ethyl acetate on silica; ν max (liquid film) 1815, 1780 and 1745$cm^{-1}$ (C=O); 250MHz, $CDCl_3$) 0.89 (6H, t, J =7Hz, 2 ×$CH_3$); 1.26-1.41 (4H, m, 2 ×$CH_2CH_3$); 1.57-1.69 (4H, m, 2 ×$CH_2CH_2CH_2$); 4.27 (4H, t, J=7Hz, 2 ×$COOCH_2$); 7.52 (1H, ddd, J =1,5,8Hz, 5-CH); 8.41 (1H, dt, J =2,8Hz, 4-CH); 8.87 (1H, dd, J =2,5Hz, 6-CH); 9.38 (1H, dd, J =1,2Hz, 2-CH).

3-[5-(3-n-Butyloxycarbonylamino-1,2,4-oxadiazol-)yl]Pyridine (0.13g) was isolated as a cream solid; $R_f$=0.45 in ethyl acetate on silica; mp 185°-187° C. (Found: C, 54.60; H, 5.38; N, 21.24; $C_{12}H_{14}N_4O_3$ requires C 54.95; M. 5.38; N, 21.36%); ν max (nujol) 3250-3000$cm^{-1}$ (NH), 750$cm^{-1}$, (C=O); δ (250MHz, $CDCl_3$) 0.90 (3H, t, J=7Hz, $CH_3$); 1.34-1.43 (2H, m, $CH_2CH_3$); 1.60-1.70 (2H, m, $CH_2CH_2CH_2$); 4.23 (2H, t, J =7Hz, $COOCH_2$); 7.44 (1H, ddd, J =1,5,8Hz, 5-CH); 8.28-8.35 (2H, m, 4-CH and NH); 8.78 (1H, dd, J =2,5Hz. 6-CH); 9.58 (1H, broad d, J =2Hz, 2-CH).

3-[5-(3-(Di-n-butyloxycarbonyl)amino-1,2,4oxadiazol)yl]]Pyridine (0.495g. 0.0014mol) Was dissolved in methanol (3ml) and a solution of sodium hydroxide (0.066%, 0.0016mol) in water (3ml) was added. After 16 hours at room temperature the methanol was evaporated and the aqueous extracted with ethyl acetate (4×25ml). The combined organics were dried (sodium sulphate) then evaporated to dryness to give 3-[5-(3-n-butyloxycarbonylamino-1,2,4-oxadiazol)-yl]Pyridine (0.255g) as a cream solid mp 185°-187° C.

c. 3-[5-(3-n-Butyloxycarbonylamino-1,2,4-oxadiazol)-yl]pyridine Methiodide

The combined batches of 3-[5-(3-n-butyloxy-carbonylamino-1,2,4-oxadiazol)-yl]Pyridine (from b) above) were suspended in dry acetone (80ml). Iodomethane (1.7ml. 0.027mol) was added and the reaction mixture was stirred at 45° C. for 1.5 days, cooled, evaporated to dryness and the residue triturated with diethyl ether to give the title compound as a yellow glass (0.51g), δ (250MHz, d$_6$DMSO) 0.94 (3H. t. J =7Hz CH$_2$CH$_3$): 1.32-1.46 (2H. m. CH$_2$CH$_3$): 1.58-1.69 (2H. m. CH$_2$CH$_2$CH$_2$): 4.16 (2H. t. J =7Hz. COOCH$_2$): 4.28 (3H s NCH$_3$); 8.34 (1H. dd. J =6.8Hz 5-CH): 9.08 (1H. d. J =8Hz. 4-CH): 9.21 (1H. d. J =6Hz 6-CH): 9.74 (1H. s. 2-CH): 11.25 (1H s. NH).

d) 3-[5-(3-n-Butyloxycarbonylamino-1,2,4-oxadiazol)-yl]-1-methyl-1.2.5.6-tetrahydropyridine Hydrogen Oxalate To a stirred, cooled (0° C.) solution of the quaternary salt (0.505g, 0.00124mol) in ethanol (10ml) and water (10ml) was added sodium borohydride (47mg, 0.00124mol) over 5 minutes. After 3 hours at room temperature the solution was evaporated and the residue Partitioned between water (10ml) and dichloromethane (25ml). The organic layer was separated and the aqueous re-extracted with dichloromethane (3×25ml). The combined organics were dried (sodium sulphate) then evaporated to dryness to give an orange gum (0.455g) which was Purified by column chromatography on silica by elution with dichloromethane/methanol (gradient elution). The title product free base was isolated as a brown gum (0.16g, 46%). R$_f$=0.42 in dichloromethane/methanol (9:1) on silica; m/e 280 for M+; δ (250MHz CDCl$_3$) 0.95 (3H, t J 7HZ CH$_2$CH$_3$) : 1.36-1.46 (2H. m. CH$_2$CH$_3$): 1.61-1.73 (2H. m CH$_2$CH$_2$CH$_2$): 2.47 (s. NCH$_3$) overlapped with 2.42-2.54 (total 5H m. 5-CH$_2$): 2.64 (2H. dd J =5Hz. 6-CH$_2$): 3.41-3.46 (2H. m. 2-CH ): 4.23 (2H. t J =7Hz. COOCH$_2$) 6.96-7.06 (1H. m. 4-CH): 8.70 (1H. broad s. NH).

The hydrogen oxalate salt had mp 68°-72° C. (propan2-ol/diethyl ether). (Found: C, 45.09; H, 5.82; N, 13.92. C$_{13}$H$_{20}$N$_4$O$_3$.1.25 C$_2$H$_2$O$_4$.1H$_2$O requires C, 45.31; H, 6.01; N, 13.64%).

EXAMPLE 25

3-[5-(3-(2-Ethyl-1-butyloxycarbonyl)amino-1,2,4-oxadiazol)-yl]quinuclidine Hydrochloride The title compound free base was obtained (700mg, 56%) from 3-[5-(3-amino-1,2,4-oxadiazol)-yl]quinuclidine (0.75g, 3.86mmol) and 2-ethyl-1-butanol (4.8, 39mmol) as described in Example 10. The Hydrochloride salt had mp 85°-87° C. (dichloromethane/ diethyl ether): (Found: C, 51.37; H, 7.59; N. 14.91. C$_{16}$H$_{26}$N$_4$O$_3$.HCl.H$_2$O requires C, 51.00; H, 7.76; N, 14.87%); m/e 322 (M+ of free base); δ (360MHz, D$_2$O) 0.87 (6H, t, J=7Hz, 2×CH$_3$); 1.36 (4H, quintet, J =7Hz, 2 ×CH$_2$CH$_3$); 1.57 (1H, septet, J =6Hz, CO$_2$CH$_2$CH); 1.80-2.00 (2H, 2.62-2.65 (1H, m, 4-CH); 3.30-3.46 (4H, m) and 3.74-3.90 (3H, m, 2-CH$_2$, 3-CH. 6-CH$_2$ and 7-CH$_2$); 4.16 (2H, d, J =6Hz, COOCH$_2$).

EXAMPLE 26

3-[5-(3-Cyclopentylpropionylamino-1,2,4-oxadiazol)-yl]quinuclidine Hydrogen Oxalate The title compound free base was obtained (0.30q. 23%) from 3-[5- -amino-1,2,4-oxadiazol)-yl]quinuclidine (0.8q 4.12mmol) and 3-cyclopentylpropionyl chloride (3.15ml, 20.6mmol) in the same manner as described for Example 1. The hydrogen oxalate salt had mp 66°-70° C. (dichloromethane/diethyl ether); (Found: C, 53.54; H, 6.65; N, 12.25. C$_{17}$H$_{26}$N$_4$O$_2$.1.4 C$_2$H$_2$O$_4$ requires C, 53.52; H, 6.53; N, 12.60%); ν max (nujol) 3600-3000 (OH,NH), 2800-2300 (NH+); 1710 (C=O, acid), 1640cm$^{-1}$ (C=O, amide); m/e 318 (M+ of free base); δ (360MHz, D$_2$O) 1.04-1.18 (2H, m, 2 ×cyclopentyl CH): 1.40-2.00 (11H. m, 3 ×cyclopentyl CH, 2 × cyclopentyl CH$_2$. COCH$_2$CH$_2$, 5-CH and 8-CH); 2.08-2.22 (2H, m, 5-CH and 8-CH); 2.53 (2H, t, J =Hz, COCH$_2$); 2.64-2.68 (1H, m, 4-CH); 3.30-3.50 (4H, m) and 3.74-3.96 (3H, m, 2-CH , 3-CH, 6-CH$_2$ and 7-CH$_2$).

EXAMPLE 27

3-[5-(3-Hexadecanoylamino-1,2,4-oxadiazol)-yl]quinuclidine

The title compound free base was obtained (170mg. 10%) from 3-[5-(3-amino-1,2,4-oxadiazol)yl quinuclidine (0.80g, 4.12mmol) and Palmitoyl chloride (5.7g, 20.6mmol) in the same manner as described for Example 1. The free base had mp 117°-119° C.; (Found: C, 69.37; H, 10.17; N, 12.51. C$_{25}$H$_{44}$N$_4$O$_2$ requires C, 69.40; H, 10.25; N, 12.95%); δ (360MHz, CDCL$_3$) 0.88 (3H, t, J 7Hz, CH$_3$); 1 20-1.40 (24H, m, (CH$_2$)$_{12}$CH$_3$); 1.40-1.56 (2H, m, COCH$_2$CH$_2$); 1.66-1.76 and 1.78-1.84 (each 2H, each m, 5-CH and 8-CH ); 2.28-2.34 (1H, m, 4-CH); 2.34-2.46 (2H, m, COCH$_2$); 2.72-2.84 (1H, m, 6-CH); 2.96-3.02 (2H, m, 7-CH$_2$); 3.12-3.26 (3H, m, 6-CH, 3-CH and 2-CH); 3.96-4.06 (1H, m, 2-CH).

EXAMPLE 28

3-5-(3-Cyclohexylacetylamino-1,2,4-oxadiazol)yl]-quinuclidine Hydrogen Oxalate

Thionyl chloride (1.6ml. 20.6mmol) was added to a solution of cyclohexylacetic acid (2.93g, 20.6mmol) in dry toluene (3ml) under nitrogen then stirred at 40°-50° C. for 2.5 hours. This cooled solution was added to a chilled solution of 3-[5-(3-amino-1,2,4-oxadiazol)-yl]quinuclidine (o.sog, 4.12mmol) and 4dimethylaminopyridine (10mg) in pyridine (30ml) under nitrogen. After 16 hours at 40° C. the reaction mixture was cooled and worked up as Example 1 to give the free base (350mg, 27%). The hydrogen oxalate salt had mp 141°-143° C.; (Found: C, 56.79; H, 7.09: N, 14.14. C$_{17}$H$_{26}$N$_4$O$_2$. 0.9 C$_2$H$_2$O$_4$ requires C, 56.53; H$_{7.02}$: N, 14.03%); δ (360MHz, D$_2$O) 1.01-1.28 (5H, m) and 1.56-1.72 (6H, m, 5 ×cyclohexyl CH$_2$, cyclohexyl CH); 1.74-1.98 (2H, m) and 2.04-2.24 (2H, m, 5-CH$_2$ and 8-CH$_2$); 2.39 (2H, d, J =7.3Hz, COCH$_2$): 2.62-2.70 (1H, m. 4-CH); 3.30-3.50 (4H, m) and 3.74-3.92 (3H, m, 2-CH$_2$, 3-CH, 6-CH$_2$ and 7-CH$_2$).

EXAMPLE 29

3-[5-(3-Isovalerylamino-1,2,4-oxadiazol)-yl]quinuclidine Sesquioxalate

The title compound free base was obtained from 3-[5-(3-amino-1,2,4-oxadiazol)-yl]quinuclidine (0.80g, 4.12mmol) and isovaleryl chloride (2.51ml, 20.6mmol) in the same manner as described for Example 1. The sesquioxalate salt had mp 137°-139° C.; (Found: C, 49.39; H, 6.07; N, 13.29. $C_{14}H_{22}N_4O_2$. 1.5 $C_2H_2O_4$ requires C, 49.39; H, 6.10; N, 13.55%);; δ (360MHz, $D_2O$) 0.97 (6H, d, J =6.7Hz. 2 ×$CH_3$); 1.80–2.00 2H, m) and 2.06–2.20 (3H, m. 5-$CH_2$, 8-$CH_2$, $CH_2CH$); 2.38 2H, d, J =7.4Hz, $COCH_2$); 2.65–2.70) 1H, m, 4-CH); 3.30–3.50 (4H, m) and 3.70–3.92 (3H, m, 2-$CH_2$, 3-CH, 6-$CH_2$ and 7-$CH_2$).

EXAMPLE 30

3-[5-(3-(2-Ethylbutyryl)amino-1,2,4-oxadiazol)yl]quinuclidine Sesquioxalate

Thionyl chloride (1.5ml. 20.5mmol) was added to a solution of 2-ethylbutyric acid (3.26ml. 25.9mmol) in dry toluene (2ml) under nitrogen then stirred at 40°–50° C. for 2 hours. This cooled solution was added to a chilled solution of 3-[5-(3-amino-1,2,4-oxadiazol)-yl]quinuclidine (0.80g, 4.12mmol) and 4-dimethylaminopyridine (10mg) in Pyridine (30ml) under nitrogen. After 16 hours at 40° C. the reaction mixture was worked up as Example 1 to give the free base (300mg, 25%). The sesquioxalate salt had mp 135°–137° C.; (Found: C, 49.90; H. 6.22; N, 12.92. $C_{15}H_{24}N_4O_2$. 1.5 $C_2H_2O_4$. 0.5$H_2O$ requires C, 49.53; H, 6.46; N. 12.83%); δ (360MHz. $D_2O$) 0.89 (6H, t, J =7.5Hz, 2 ×$CH_2$); 1.57–1.66 (4H, m, 2 ×CH ); 1.82–2.00 (2H, m) and 2.10–2.24 (2H, m, 5-$CH_2$ and 8-$CH_2$); 2.38–2.68 (1H, m, COCH); 2.64–2.70 (1H, m, 4-CH); 3.32–3.52 (4H, m) and 3.76–3.96 (3H, m, 2-$CH_2$, 3-CH, 6-CH and 7-$CH_2$).

EXAMPLE 31

3-[5-(3-Heptan-4-oxycarbonylamino-1,2,4-oxadiazol)-yl]quinuclidine Hydrogen Oxalate The title compound free base was obtained from 3-[5-(3-amino-1,2,4-oxadiazol)-yl]quinuclidine (2.0g, 10.3mmol) and 4-heptanol (14.5ml. 100.2mmol) in a manner similar to Example 17 except that the formation of the chloroformate was carried out at −40° C. The hydrogen oxalate salt had mp 165°–167° C.; (Found: C, 53.38; H, 6.88; N, 13.19. $C_{17}H_{28}N_4O_3$. $C_2H_2O_4$ requires C, 53.51; N, 13.14%); δ (360MHz, $D_2O$) 0.89 (6H, t, J =7.4Hz, 2 ×$CH_2$), 1.28–1.44 (4H, m, 2 ×$CH_2CH_3$); 1.56–1.70 (4H, m, 2 ×$CH_2CH_2$); 1.80–2.00 (2H, m) and 2.08–2.12 (2H, m, 5-$CH_2$ and 8-$CH_2$); 2.62–2.68 (1H, m, 4-CH); 3.30–3.50 (4H, m) and 3 74–3.90 (3H, m, 2-$CH_2$, 3-CH, 6-$CH_2$ and 7-$CH_2$). 4.90–4.96 (1H, m, $CO_2CH$).

EXAMPLE 32

3-[5-(3-(1-Ethoxycarbonylpropan-2-oxycarbonyl) amino-1,2,4-oxadiazol)-yl]quinuclidine Hydrogen Oxalate The title compound free base was obtained (610mg. from 3-[5-(3-amino-1,2,4-oxadiazol)-yl]quinuclidine (0.86g, 4.4mmol) and ethyl-3-hydroxybutyrate (5.74ml, 43.9mmol) in the same manner as described for Example 17. The hydrogen oxalate salt had mp 126° C. (dec); (Found: C, 47.95; H, 5.62; N, 12.38. $C_{16}H_{24}N_4O_5$. 1.2 $C_2H_2O_4$ requires H, 5.78; N, 12.17%) δ (360MHz, $D_2O$) 3H t, J =7.1Mz, $CO_2CH_2CH_3$); 1 37 (3H, d. J =6.4Hz, CHCH_3); 1.80–1.98 (2H, m) and 2H, m, 5-$CH_2$ and 8-$CH_2$; 2.62–2.68 m, 4-CH); 2.75 (2H, dd, J =5.7, 7.4Hz. $CHCH_2CO_2$); 3.32–3.48 (4H, m) and 3.76–3.92 (3H, m, 2-$CH_2$, 3-CH, 6-$CH_2$ and 7-$CH_2$; 4.08–4.22 (2H, m, $CO_2CH_2CH_3$); 5.24–5.30 (1H, m, $CO_2CH$).

EXAMPLE 33

3-[5-(3-Phenylacetamido-1,2,4-oxadiazol)-yl]quinuclidine Hydrogen Oxalate

Reaction of 3-[5-(3-amino-1,2,4-oxadiazol)-yl]quinuclidine (810mg, 4.17mmol) with Phenylacetyl chloride (2.7ml. 20.4mmol), by the method of Example gave the title compound (55mg). mp 134°–137° C.; Found: C, 58.00; H, 5.77; N, 14.52.$C_{17}H_{20}N_4O_2$. 0.8$(COOH)_2$ requires C, 58.12; H, 5.66; N, 14.57%); m/e 312 ($M^+$ of free base); δ (360MHz, $D_2O$) 1.78–1.97 and 2.05–2.23 (each 2H, each m, 5$CH_2$ and 8$CH_2$), 2.60–2.68 (1H, m, 4CH), 3.30–3.48 (4H, m. 6$CH_2$ and 7$CH_2$), 3.73–3.91 (3H, m, 2$CH_2$ and 3CH), 3.89 (2H, s, $CH_2CO$) and 7.28–7.46 (5H, m, Ph).

EXAMPLE 34

3-[5-(3-Cyclohexylcarbonylamino-1,2,4-oxadiazol)yl]-quinuclidine Hydrogen Oxalate Reaction of 3-[5-(3-amino-1,2,4-oxadiazol)-yl]quinuclidine (873mg, 4.5mmol) with cyclohexylcarbonyl chloride (3.0ml, 22.5mmol) by the method of Example 1 gave the title compound (135mg). mp 164°–166° C.: (Found: C. 54.02; H 6.67; N. 13.81. $C_{16}H_{24}N_4O_2$ $(COOH)_2$.0.25$H_2O$ requires C, 54.19; H, 6.69; N, 14.04%); m/e 304 ($M^+$ of free base); δ (360MHz $D_2O$) 1.15–1.50, 1.64–2.00 and 2.04–2.25 (5H, 7H and 2H respectively, each m, 5$CH_2$, 8$CH_2$ and 5 ×$CH_2$ of cyclohexyl), 2.45–2.56 (1H, m, CHCO), 2.63–2.69 (1H, m, 4CH), 3.30–3.50 (4H, m, 6$CH_2$ and 7$CH_2$) and 3.74–3.92 (3H, m, 2$CH_2$ and 3CH).

EXAMPLE 35

3-[5-(3-(2,2-Dimethyl)butyrylamino-1,2,4-oxadiazol)-ylyl]quinuclidine Hydrogen Oxalate.

Reaction of 3-[5-(3-amino-1,2,4-oxadiazol)-yl]quinuclidine (792mg. 4.1mmol) with 2.2-dimethylbutyryl chloride (2.8ml, 20.4mmol) by the method of Example 1 gave the title compound (147mg), mp 134°–136° C.; (Found: C, 52.73; H, 6.76; N, 14.40. $C_{15}H_{24}N_4O_2$.-$(COOH)_2$. 0.25$H_2O$ requires C, 52.77; H, 6.90; N, 14.48%); m/e 295 ($CI^+$ $M+1]^+$ of free base); δ 360MHz, $D_2O$) 1.05 (9H, s. 3 ×$CH_3$, 1.80–1.98 and 2.06–2.24 (each 2H, each m, 5$CH_2$ and 8$CH_2$, 2.37 (2H, s, $CH_2CO$), 2.63–2.69 (1H, m, 4CH), 3.32–3.50 4H, m, 6$CH_2$ and 7$CH_2$) and 3.74–3.92 (3H, m, 2$CH_2$ and 3CH).

EXAMPLE 36

3-[5-(3-(2-Methoxycarbonyl-2-methyl)propyl-1-oxycarbonylamino-1,2,4-oxadiazol)-yl]quinuclidine Hydrochloride Reaction of 3-[5-(3-amino-1,2,4-oxadiazol)-yl]quinuclidine (1.0g, 5.1mmol) with 2-methoxycarbonyl2-methylpropan-1-ol (5.0ml, 39.5mmol) by the method of Example 10 gave the title compound (482mg). mp 205°–209° C.; (Found: C, 49.20; H, 6.42; N, 14.69. $C_{16}H_{24}N_4O_5$.HCl requires C. 49.42; H, 6.48; N, 14.40%); m/e 352 ($M^+$ of free base); δ (360MHz, $D_2O$) 1.27 (6H, s, 2 ×$CH_3$) 1.82–2.00 and 2.08–2.20 (each 2H, each, m, 5$CH_2$ and 8$CH_2$). 2.64–2.69 (1H, m, 4CH), 3.33–3.54 (4H, m, 6CH$_2$ and 7CH$_2$), 3.73 (3H, s, OCH$_3$), 3.78–3.92 (3H, m, 2CH$_2$) and 3CH) and 4.30 (2H, s, OCH$_2$).

EXAMPLE 37

3-5-(3-n-Hexyloxycarbonylamino-1,2,4-oxadiazol)yl]-quinuclidine

This Was obtained (250mg, 32%) from 3-[5-(3-amino1,2,4-oxadiazol)-yl]quinuclidine (0.46g, 2.4mmol) and n-hexylchloroformate (3.9ml, 24mmol) as given in Example 5, except that the reaction mixture was stirred at 4° C. for 16 hours followed by 6 hours at room temperature. The Product had mp 131°–132° C.; (Found: C, 59.04; H, 8.01; N, 16.93. C$_{16}$H$_{26}$N$_4$O$_3$ 0.2H$_2$O requires C, 53.95; H, 8.16; N, 17.19%); m/e 322 (M+); 360MHz, CDCl$_3$) 0.90 (3H, t, J =7Hz, CH$_3$; 1.22–1.52 (8H, m, COOCH$_2$ ); 1.62–1.84 (4H, m, 5CH$_2$ and 8CH$_2$; 2.26–2.34 (1H, m, 4CH); 2.72–2.80, 2.90–3.06 and 3.06–3.22 (1H, 2H and 3H respectively, each m, 2CH, 3CH, 6CH$_2$ and 7CH$_2$); 4.08 (1H, d, J=11Hz, 2CH); 4.18 (2H, t, J =7Hz, COOCH$_2$); 11.98 (1H, broad s, NH).

EXAMPLE 38

3-[5-(3-n-Butyloxycarbonylamino-1,2,4-oxadiazol)yl]-1,2,5,6-tetrahydropyridine Hydrochloride Vinyl chloroformate (0.15ml, 0.15mmol) was added to a stirred, cooled (−5° C.) solution of 3-[5-(3-n-butyloxycarbonylamino-1,2,4-oxadiazol)-yl]-1-methyl1.2 5.6-tetrahydropyridine (35mg. 0.12mmol) and tetrabutylammonium iodide (1mg) in 1.2-dichloroethane (5ml). The solution was heated to reflux for 30 minutes, cooled, water (5ml) added and the organic layer separated. The aqueous was re-extracted with dichloromethane (3×10 ml) and the combined organics dried (sodium sulphate) then evaporated to dryness. The residue was dissolved in saturated methanolic hydrogen chloride (5ml) and after 16 hours evaporated and treated with propan-2-ol/diethyl ether to afford the title compound as a hygroscopic product (12mg); m/e 267 (CI+) for (M+H)+ of free base; (CI−, Found: (M-H)− 265.1298, (M-H) C$_{12}$H$_{17}$N$_4$O$_3$ requires 265.1301).

EXAMPLE 39

3-[5-(3-Octanyloxycarbonylamino-1 2.4-oxadiazol)yl]-1-azabicyclo[2.2.1heptane Hydrogen Oxalate To a stirred solution of 3-[5-(3-amino-1,2,4-oxadiazol)-yl]-1-azabicyclo[2.2.1]-heptane (120mg, 0.66mmol) in anhydrous dichloromethane (1ml) and pyridine (104mg, 1.32mmol, dried over potassium hydroxide) at room temperature was added n-octyl chloroformate (254mg, 1.32mmol) and 4-dimethyl aminopyridine (2mg) and the solution stirred overnight. Solvents were evaporated and the residue Partitioned between dichloromethane and 5% aqueous potassium carbonate. The organic layer was separated, dried, evaporated and the residue chromatographed on a pre-packed normal Phase silica column using chloroform as eluant to afford the title compound as free base, which was treated with anhydrous oxalic acid in diethyl ether to give the hydrogen oxalate salt (60mg) mp 133°–136° C. (diethyl ether/hexane). (CI−, Found (M-H)− 335.2086. C$_{17}$H$_{27}$N$_4$O$_3$ requires (M-H) 335.2083); δ (250MHz, CDCl$_3$) 0.88 (3H, t, J=7Hz, CH$_3$); 1.20–1.40 (10H, m, ); 1.50–1.68 (2H, m, COOCH$_2$CH$_2$); 1.80–1.92 (1H m, 5-CH); 2.08–2.24 (1H, m, 5-CH; 3.10–3.96 (8H, m, 2-CH$_2$, 3-CH, 4-CH. 6-CH$_2$ and 7-CH$_2$); 4.08 (2H, t, J =7Hz, COOCH$_2$).

EXAMPLE 40

Tablet Preparation

Tablets containing 1.0, 2.0, 25.0, 26.0, 50.0 and 100.0 mg., respectively, of the following compounds are prepared as illustrated below:
3-[5-(3-Octanoylamino-1,2,4-oxadiazol)-yl]quinuclidine:
3-[5-(3-Octanyloxycarbonylamino-1,2,4-oxadiazol)-yl]quinuclidine:
3-[5-(3-n-Butyloxycarbonylamino-1,2,4-oxadiazol)-yl]-1-methyl-1,2,5,6-tetrahydropyridine
3-[5-(3-Octanyloxyamino-1,2,4-oxadiazol)-yl]-1-azabicyclo-[2.2.1]-heptane

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, and 100.0 mg of active ingredient per tablet.

What is claimed is:

1. An oxadiazole compound or a pharmaceutically acceptable salt thereof represented by formula (II):

$$\text{(II)}$$

wherein
R$^1$ represents a non-aromatic azacyclic or azabicyclic ring system, excluding 1-azabicyclic systems which are substituted to the oxadiazole compound at the bridgehead position; and
R$^2$ represents a substituent which is convertible in vivo to an amino group of formula —NH.Q, wherein Q is selected from the group consisting of CHO, COR and CO$_2$R and R is selected from an unsubstituted hydrocarbon group having up to 20 carbon atoms and a hydrocarbon group having up to 20 carbon atoms substituted with a substituent selected from the group consisting of amino, C$_{1-6}$alkylthio, arylthio, sulphamoyl, carbamoyl, amidino, guanidino, nitro, chloro, bromo, fluoro, carboxy, $C_{1-6}$alkoxycarbonyl, $C_{1-6}$alkylcarbonyl, $C_{1-6}$alkylcarbonyloxy, arylcarbonyl and -mono-di- and tri($C_{1-6}$)alkylamino.

2. The compound according to claim 1, wherein the azacyclic or azabicyclic ring system is selected from the group consisting of pyrrolidine; 1,2,5,6-tetrahydropyridine; quinuclidine and 1-azabicyclo[2.2.1]heptane, unsubstituted or substituted with a group selected from methyl and hydroxy.

3. The compound according to claim 1 wherein $R^2$ represents a group of formula —NH.Q, wherein Q is selected from the group consisting of CHO, COR and $CO_2R$, and R is selected from $C_{1-10}$alkyl, phenyl, cyclohexyl, fluorenylmethyl, phenyl($C_{1-6}$)alkyl, cyclohexylmethyl and $C_{1-6}$ alkoxycarbonyl($C_{1-6}$)alkyl.

4. The compound according to claim 1 selected from:
3-[5-(3-octanoylamino-1,2,4-oxadiazol)-yl]quinuclidine;
3-[5-(3-benzoylamino-1,2,4-oxadiazol)-yl]quinuclidine;
3-[5-(3-isobutyrylamino-1,2,4-oxadiazol)-yl]quinuclidine;
3-[5-(3-(2,2-dimethylpropionyl)amino-1,2,4-oxadiazol)-yl]quinuclidine;
3-[5-(3-ethoxycarbonylamino-1,2,4-oxadiazol)yl]-quinuclidine;
3-[5-(3-iso-propoxycarbonylamino-1,2,4-oxadiazol)-yl]quinuclidine;
3-[5-(3-t-butoxycarbonylamino-1,2,4-oxadiazol)-yl]quinuclidine;
3-[5-(3-iso-butoxycarbonylamino-1,2,4-oxadiazol)-yl]quinuclidine;
3-[5-(3-(9-fluorenyl)methoxycarbonylamino-1,2,4-oxadiazol)-yl]quinuclidine;
3-[5-(3-cyclohexylmethoxycarbonylamino-1,2,4-oxadiazol)-yl]quinuclidine;
3-[5-(2,2-dimethylprop-1-oxycarbonylamino-1,2,4-oxadiazol)-yl]quinuclidine;
3-[5-(3-cyclohexyloxycarbonylamino-1,2,4-oxadiazol)-yl]quinuclidine;
3-[5-(3-octyloxycarbonylamino-1,2,4-oxadiazol)-yl]quinuclidine;
DL-3-[5-(3-(1-(3-n-pentyloxycarbonyl)-1-ethoxycarbonylamino)-1,2,4-oxadiazol)-yl]quinuclidine;
3-[5-(3-(3-phenylprop-1-oxycarbonylamino-1,2,4-oxadiazol)-yl]quinuclidine;
3-[5-(3,3-dimethylbut-1-oxycarbonylamino-1,2,4-oxadiazol)-yl]quinuclidine;
3-[5-(3-pent-3-yloxycarbonylamino-1,2,4-oxadiazol)-yl]quinuclidine;
3-[5-(3-(2-propylpent-1-yloxycarbonylamino)-1,2,4-oxadiazol)-yl]quinuclidine;
3-[5-(3-acetamido-1,2,4-oxadiazol)-yl]quinuclidine;
3-[5-(3-formamido-1,2,4-oxadiazol)-yl]quinuclidine;
3-[5-(3-butyloxycarbonylamino-1,2,4-oxadiazol)-yl]quinuclidine;
3-[5-(3-(4-methyl-1-pentyloxycarbonylamino)-1,2,4-oxadiazol)-yl]quinuclidine;
3-[5-(3-(4-cyclohexylbutyloxycarbonylamino)-1,2,4-oxadiazol)-yl]quinuclidine;
3-[5-(3-n-butyloxycarbonylamino-1,2,4-oxadiazol)-yl]-1-methyl-1,2,5,6-tetrahydropyridine;
3-[5-(3-(2-ethyl-1-butyloxycarbonyl)amino-1,2,4-oxadiazol)-yl]quinuclidine;
3-[5-(3-cyclopentylpropionylamino-1,2,4-oxadiazol)-yl]quinuclidine;
3-[5-(3-hexadecanoylamino-1,2,4-oxadiazol)yl]quinuclidine;
3-[5-(3-cyclohexylacetylamino-1,2,4-oxadiazol)-yl]quinuclidine;
3-[5-(3-isovalerylamino-1,2,4-oxadiazol)yl]quinuclidine;
3-[5-(3-(2-ethylbutyryl)amino-1,2,4-oxadiazol)-yl]quinuclidine;
3-[5-(3-heptyl-4-oxycarbonylamino-1,2,4-oxadiazol)-yl]quinuclidine;
3-[5-(3-(1-ethoxycarbonylprop-2-oxycarbonyl)amino-1,2,4-oxadiazol)-yl]quinuclidine;
3-[5-(3-phenylacetamido-1,2,4-oxadiazol)yl]quinuclidine;
3-[5-(3-cyclohexylcarbonylamino-1,2,4-oxadiazol)-yl]quinuclidine;
3-[5-(3-(2,2-dimethyl)butyrylamino-1,2,4-oxadiazol)-yl]quinuclidine;
3-[5-(3-(2-methoxycarbonyl-2-methyl)propyl-1-oxycarbonylamino-1,2,4-oxadiazol)yl]quinuclidine;
3-[5-(3-n-hexyloxycarbonylamino-1,2,4-oxadiazol)-yl]quinuclidine;
3-[5-(3-n-butyloxycarbonylamino-1,2,4-oxadiazol)-yl]-1,2,5,6-tetrahydropyridine;
3-[5-(3-octanyloxycarbonylamino-1,2,4-oxadiazol)-yl]-1-azabicyclo[2.2.1]heptane;
and salts thereof.

5. A pharmaceutical composition which comprises a pharmaceutically acceptable carrier and an effective amount of a compound according to claim 1.

6. A method for the treatment of neurological and mental disorders whose clinical manifestations are due to involvement of specific populations of cholinergic neurones, which method comprises administering to a patient in need of such treatment an effective central muscarinic agonist amount of a compound according to claim 1.

7. A method for treating a patient suffering from a painful condition which comprises administering to said patient an effective analgesic amount of a compound according to claim 1.

* * * * *